United States Patent
Burns

(10) Patent No.: US 7,038,068 B2
(45) Date of Patent: May 2, 2006

(54) METHOD FOR LIQUID/LIQUID EXTRACTION OF MOLECULAR WEIGHT FRACTIONS OF PERFLUORINATED POLYETHERS

(75) Inventor: John M. Burns, Morgan Hill, CA (US)

(73) Assignee: Hitachi Global Storage Technologies Netherlands B.V., Amsterdam (NL)

( * ) Notice: Subject to any disclaimer, the term of this patent is extended or adjusted under 35 U.S.C. 154(b) by 97 days.

(21) Appl. No.: 10/802,164

(22) Filed: Mar. 16, 2004

(65) Prior Publication Data

US 2005/0209468 A1    Sep. 22, 2005

(51) Int. Cl.
*C07D 307/02*    (2006.01)

(52) U.S. Cl. .................. 549/504; 568/815; 204/157.69

(58) Field of Classification Search ............... 568/815; 549/445; 204/157.69
See application file for complete search history.

(56) References Cited

U.S. PATENT DOCUMENTS

| | | | |
|---|---|---|---|
| 3,242,216 A | 3/1966 | Miller et al. | |
| 3,665,041 A | 5/1972 | Sianasi et al. | |
| 3,715,378 A | 2/1973 | Belardinelli et al. | |
| 4,267,238 A | 5/1981 | Chernega | |
| 4,268,556 A | 5/1981 | Pedrotty | |
| 4,721,795 A | 1/1988 | Caporiccio et al. | |
| 5,292,585 A | 3/1994 | Ohnuki et al. | |
| 5,663,127 A | 9/1997 | Flynn et al. | |
| 5,910,614 A * | 6/1999 | Turri et al. | 568/615 |

OTHER PUBLICATIONS

Curran, "Strategy-level separations in organic systhesis", Angew. Chem.Int. Ed. (1998), vol. 37,pp. 1175-1190, 1194-1196.*

* cited by examiner

*Primary Examiner*—Kamal A. Saeed
(74) *Attorney, Agent, or Firm*—Thomas R. Berthold

(57) ABSTRACT

A liquid/liquid extraction method is used for separating a perfluorinated polyether (PFPE) into two molecular-weight distributions using an alcohol or cyclic ether as one solvent and a fluorinated solvent as the other solvent. The more polar alcohol or cyclic ether solvent extracts the lower molecular weight PFPE and the less polar fluorinated solvent extracts the higher molecular weight PFPE. In addition, when the PFPE is a mixture of PFPEs with different end groups, such as a mixture of predominantly Z-Tetraol but with other PFPEs with Z-Dol end groups, there is an enrichment of the Z-Tetraol in the more polar solvent. The preferred PFPE is a mixture of PFPEs in as-purchased Z-Tetraol and the preferred solvents are methanol or trifluoroethanol as one solvent and a perfluorinated hydrocarbon, such as perfluorohexane, as the other solvent.

9 Claims, 2 Drawing Sheets

METHOD FOR LIQUID/LIQUID EXTRACTION OF MOLECULAR WEIGHT FRACTIONS OF PERFLUORINATED POLYETHERS

TECHNICAL FIELD

This invention relates generally to methods for isolating the molecular weights of perfluorinated polyethers usable as magnetic recording disk lubricants.

BACKGROUND OF THE INVENTION

In a magnetic recording disk drive, data is stored in a thin magnetic layer on the disk. Data is written to and read from the disk by a read/write head on a head carrier or slider that is maintained in close proximity to the rotating disk.

The magnetic recording disk typically comprises a substrate, such as an aluminum-magnesium (AlMg) alloy disk blank with a nickel-phosphorous (NiP) surface coating or a chemically-strengthened glass disk blank, a cobalt-based alloy magnetic layer, and a protective overcoat of amorphous carbon, hydrogenated-carbon and/or nitrogenated-carbon for corrosion resistance and wear resistance from the slider. A liquid lubricant is also maintained on the carbon overcoat to prevent damage to the head and the disk during starting and stopping of the disk and inadvertent contact of the slider with the disk. The lubricant is typically applied by dipping the disk into a solution of the lubricant in a fluorinated solvent and then evaporating the solvent. During normal operation of the disk drive, wear is prevented by lubricant reflow onto regions of the disk from which lubricant has been removed by sporadic contacts with the slider.

The conventional disk lubricants comprise mixtures of long chain polymers characterized by a wide distribution of molecular weights and include perfluoropolyethers, functionalized perfluoropolyethers, perfluoropolyalkylethers (PFPE), and functionalized PFPE. The PFPE lubricants have polar hydroxyl end groups that physisorb and chemisorb on the carbon overcoat. Within the context of magnetic recording, chemisorbed lubricant is the lubricant that remains on the carbon overcoat after rinsing with solvent.

One problem with the lubricants is that they tend to deplete due to air shear forces, mechanical shear forces from the slider, and spin-off from centrifugal forces during operation of the disk drive. To address this problem certain PFPE lubricants are available that have a relatively high molecular weight (MW), e.g., greater than 2500, to increase the viscosity and thus decrease the tendency to spin off the disk. An example of this type of lubricant is a Z-Dol manufactured by Solvay Solexis Sp.A., Italy. Z-Dol-type lubricants have dual functionality with 1° hydroxyl end groups and are random copolymers of perfluoromethylene, ethylene, propylene, and butylene oxide. Since the lubricant chain contains very little perfluoropylene and butylene oxide, the general structural formula for a Z-Dol is given by:

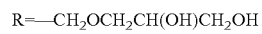

where m and n are integers and R=—CH$_2$OH.

The performance of Z-Dol-lubricated disks can be improved if the molecular weight of the Z-Dol applied to the disks can be controlled. Conventional well-known extraction processes for isolating specific molecular weight fractions of the Z-Dol to be applied to the disks are distillation and supercritical fluid extraction. Liquid/liquid extraction is a separation process that takes advantage of the relative solubilities of solutes in immiscible solvents. The solute dissolves more readily and becomes more concentrated in the solvent in which it has a higher solubility. A partial separation occurs when a number of solutes have different relative solubilities in the two solvents used. In U.S. Pat. No. 5,292,585, liquid/liquid extraction has been proposed for a Z-Dol derivative, AM-2001, for removing impurities and low molecular weight AM-2001 using an ester and an alcohol as the solvents, with the high molecular weight AM-2001 being generally insoluble in the alcohol.

However, with the increase in disk drive operating speeds to 10,000 RPM and higher, lubricants such as Z-Dol and AM-2001 cannot be sufficiently prevented from the effects of high mechanical shear, high air shear and centrifugal forces. Thus, newer PFPE lubricants have been proposed, such as Z-Tetraol, also manufactured by Solvay Solexis, in which the adhesion force of the lubricant to the carbon overcoat is made stronger by increasing the polarity of the functional end group. Z-Tetraol has mostly di-hydroxyl end groups consisting of 1° and 2° hydroxyl groups. The general structural formula for Z-Tetraol is the same as for Z-Dol but the end group is given by:

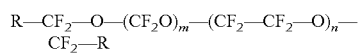

Z-Tetraol as purchased from the manufacturer has a wide distribution of molecular weights. Z-Tetraol is derived from Z-Dol by addition of glycidol onto the Z-Dol end-groups. Typically only about 85% of the as-purchased Z-Tetraol has the desired di-hydroxyl end groups, with the remainder having the Z-Dol end group. As a result, disks lubricated with as-purchased Z-Tetraol will have lubricant having a mix of Z-Tetraol and Z-Dol end groups.

Thus isolation of the Z-Tetraol end groups and isolation of specific molecular weight fractions of Z-Tetraol from the as-purchased Z-Tetraol are desired. Higher molecular weight Z-Tetraol may be desirable, while Z-Tetraol with a higher percentage of di-hydroxyl end groups is desirable to improve the consistency and tenacity of the bonding of the lubricant to the carbon overcoat across the disk. In addition, low molecular weight Z-Tetraol has a higher volatility and may be desirable for disk manufacturing where the lubricant is applied to the disks in the vapor phase, as an alternative to the conventional dipping method.

SUMMARY OF THE INVENTION

The invention is a liquid/liquid extraction method for separating a perfluorinated polyether (PFPE) into two molecular-weight distributions using an alcohol or cyclic ether as one solvent and a fluorinated solvent as the other solvent. The more polar alcohol or cyclic ether solvent extracts the lower molecular weight PFPE and the less polar fluorinated solvent extracts the higher molecular weight PFPE. In addition, when the PFPE is a mixture of PFPEs with different end groups, such as a mixture of predominantly Z-Tetraol but with other PFPEs with Z-Dol end groups, there is an enrichment of the Z-Tetraol in the more polar solvent. The preferred PFPE is a mixture of PFPEs in as-purchased Z-Tetraol and the preferred solvents are methanol or trifluoroethanol as one solvent and a perfluorinated hydrocarbon, such as perfluorohexane, as the other solvent.

For a fuller understanding of the nature and advantages of the present invention, reference should be made to the following detailed description taken together with the accompanying figures.

DETAILED DESCRIPTION OF THE INVENTION

Figure 1:
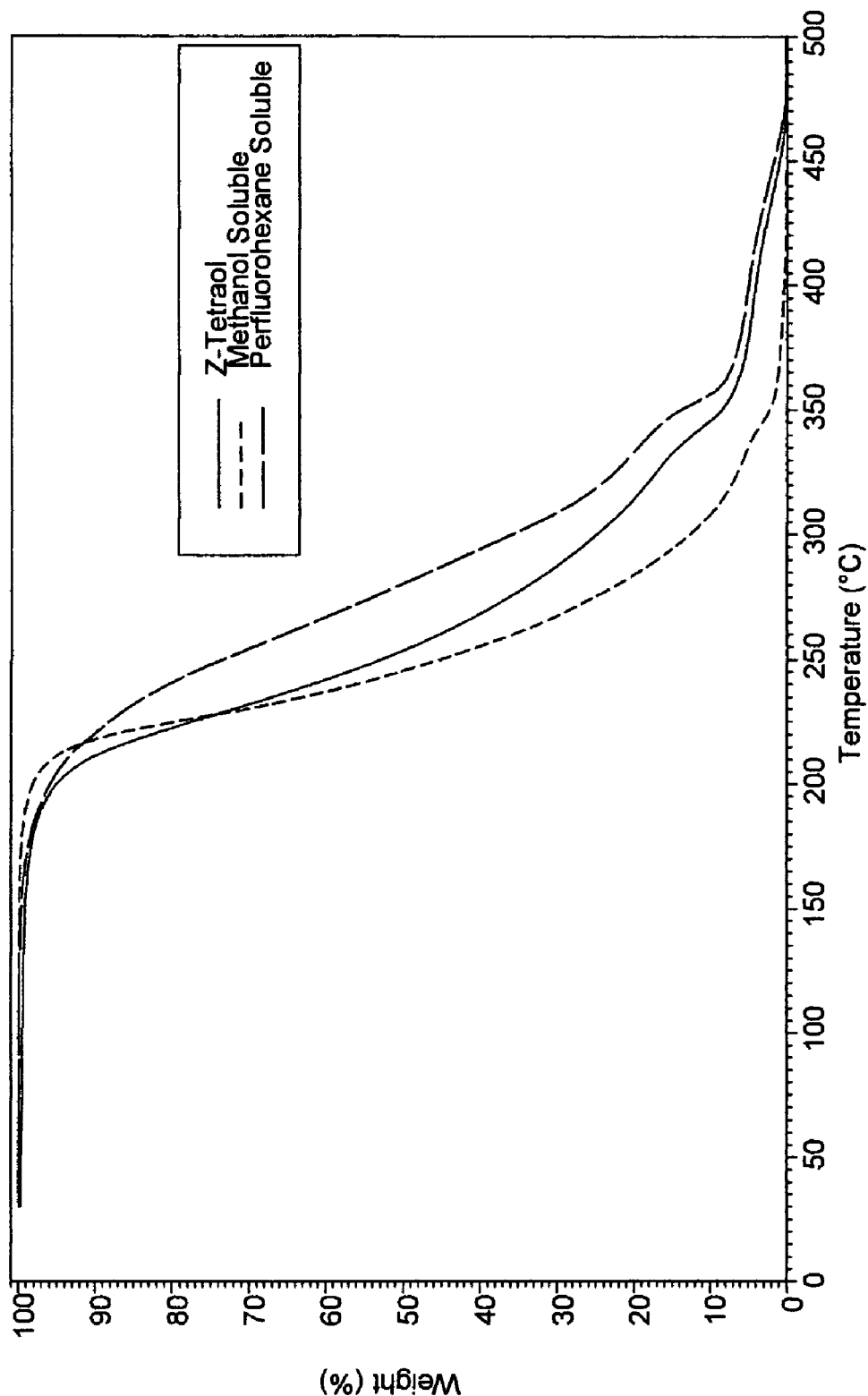
FIG. 1 is a thermogravimetric analysis curve comparing the molecular weight distribution of the virgin Z-Tetraol, the methanol-soluble fraction and the perfluorohexane-soluble fraction for Example 1.

The definitions set forth herein apply only to the terms as they are used in this patent and may not be applicable to the same terms as used elsewhere, for example in the scientific literature or other patents. The following descriptions of the preferred embodiments and examples are provided by way of explanation and illustration. As such they are not intended to limit the scope of the invention as defined by the claims.

The present invention relates to a liquid/liquid extraction method for PFPEs using an alcohol or cyclic ether, or mixtures thereof, as one solvent and a fluorinated solvent, or mixtures thereof, as the other solvent. The more polar alcohol or cyclic ether solvent extracts the lower molecular weight PFPE and the less polar fluorinated solvent extracts the higher molecular weight PFPE. In addition, when the PFPE is a mixture of PFPEs with different end groups, such as a mixture of predominantly Z-Tetraol but with other PFPEs with Z-Dol end groups, there is an enrichment of the Z-Tetraol in the more polar solvent.

Perfluorinated Polyethers

Perfluorinated polyether polymers are fluorinated oligomers, homopolymers and copolymers of polyethers. Suitable perfluorinated polyethers for use in the methods of the invention include commercially available highly functionalized polar perfluorinated polyethers ("PFPE") such as Fomblin® Z-Tetraol, Fomblin® Z-Dol TX (Solvay Solexis, Sp.A., Italy) plus other highly functionalized polar derivatives of PFPEs. Other PFPEs are well known and described in the literature. See for example, U.S. Pat. No. 3,242,218 to Miller; U.S. Pat. No. 3,665,041 to Sianesi; U.S. Pat. No. 3,715,378 to Sianesi et al.; U.S. Pat. No. 4,268,556 to Pedrotty; U.S. Pat. No. 4,267,238 to Chernega; U.S. Pat. No. 4,721,795 to Caporiccio et al.; and U.S. Pat. No. 5,663,127 to Flynn et al. The term "perfluorinated polyether" is also intended to include non-functionalized polar PFPEs that are purchased and functionalized prior to use. These include PFPEs such as those sold under the brand names KrytoX® (DuPont Specialty Chemicals, Deepwater, N.J.), Demnum® (Daikin Kogyo Co., Ltd., Japan), and other PFPEs sold under the Fomblin® Z name.

The PFPEs described in U.S. Pat. No. 5,663,127 to Flynn et al. are particularly well suited for, and benefit from, use in the methods of the invention. They are described as being perfluoropolyether compounds represented by the formula:

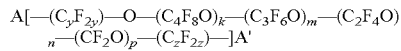

$A[—(C_yF_{2y})—O—(C_4F_8O)_k—(C_3F_6O)_m—(C_2F_4O)_n—(CF_2O)_p—(C_zF_{2z})—]A'$

The terminal A and A' moieties are monovalent organic groups such as $—CF_2CF_3$, $—CF_3$, $—F$, $—OCF_2CF_3$, $—OCF_3$, $—CF_2C(O)F$, $—C(O)F$, alkyl, aryl and alkylaryl groups. The integers y and z can range from 0–20, while the integers k, m, n, and p can range from 0–200, with the sum of k, m, n, and p typically being 2–200. The repeating units can be randomly distributed in the backbone of the compound. The end groups $C_yF_{2y}$ and $C_zF_{2z}$, and the internal groups $C_4F_8O$, $C_3F_6O$, and $C_2F_4O$, can all be linear or branched.

Other PFPEs that can benefit from the methods of the invention are described below.

Krytox® has the structure:

$F_3C—CF_2—CF_2—O—[CF(CF_3)—CF_2—O]_m—CF_2—CF_3$, where m is about 4 or 5, and is synthesized by base-catalyzed polymerization of hexafluoropropylene oxide, as described by Gumbrecht, ASLE Trans. 9:24 (1966). The hydrogen atoms in the resulting polymer are then replaced by fluorine atoms by subsequent contact with F2 in solution, as described by Ohsaka, Petrotech (Tokyo) 8:840 (1985).

Demnum® has the structure: $F_3C—CF_2—CF_2—O—[CF_2—CF_2—O]_m—CF_2—CF_3$, where m is about 4 or 5, and is made in a manner similar to that for Krytox®, but starting with 2,2,3,3-tetrafluorooxetane.

Fomblin® Z has the structure: $F_3C—O—[CF_2—CF_2—O]_m—[CF_2—O]_n—CF_3$, where m and n are about 4 or 5, and is synthesized by photooxidation of tetrafluoroethylene and is a linear, random copolymer of ethylene oxide and methylene oxide units; see Sianesi, Chim. Ind. 55:208 (1973).

These PFPEs are also available with carboxylic acid end groups, as exemplified by Krytox®-H, Demnum®-SH, and Fomblin® Z-DIAC.

Alcohols and Cyclic Ethers

Suitable alcohols useful as the first and more polar solvent in the methods of the invention include by way of illustration and not limitation, lower alcohols such as methanol, ethanol, propanol, isopropanol, butanol, pentanol and hexanol; and halogenated alcohols such as trifluoroethanol, pentafluoropropanol and heptafluorobutanol.

Suitable cyclic ethers useful as the first and more polar solvent in the methods of the invention can either be saturated or unsaturated and will preferably not contain any fluorine atoms. Exemplary cyclic ethers include by way of illustration and not limitation, tetrahydrofuran, 2-methyltetrahydrofuran, furan, tetrahydropyran, pyran, and dioxane. Saturated cyclic ethers such as tetrahydrofuran, 2-methyltetrahydrofuran, tetrahydropyran, and dioxane are preferred.

The first solvent may also be a mixture of more than one alcohol, a mixture of more than one nonfluorinated cyclic ethers, or a mixture of an alcohol with a nonfluorinated cyclic ether.

Highly Fluorinated Solvents

Perfluorinated solvents are fluorinated hydrocarbons, typically compounds having carbon atoms substituted with one or more fluorine atoms. The backbone can be straight, branched, or cyclic. The backbone may also be substituted with other halogen atoms such as chlorine, bromine and iodine. The backbone can consist entirely of carbon atoms or may have one or more heteroatoms such as $—O—$, $—NR—$ (where R can be H or a functional group such as alkyl), $—S—$, and so forth.

In general, fluorinated solvents useful as the second and less polar solvent in the methods of the invention include, by way of illustration and not limitation, relatively non-polar solvents such as perfluorinated hydrocarbons ("PFC") hydrochlorofluorocarbons ("HCFC"), hydrofluoroethers ("HFE"), hydrofluorocarbons ("HFC"), hydrohalofluoroethers ("HHFE"), perfluorinated amines and perfluorinated cyclic ethers. The PFCs include certain Fluorinert® solvents from 3M, such as FC-72.

Examples of HCFCs include chlorofluoroalkanes such as dichloropentafluoropropanes (e.g., 2,3-dichloro-1,1,1,3-3-pentafluoropropane); trichlorotrifluoroethanes (e.g., 1,1,2-trichloro-1,2,2-trifluoroethane); and dichlorotrifluoroethanes (1,1-dichloro-2,2,2-trifluoroethane, 1,1-dichloro-1,2,2-trifluoroethane and 1,2-dichloro-1,1,2-trifluoroethane).

HFEs are also referred to as highly fluorinated ethers, and are generally fluorinated hydrocarbons where the carbon backbone includes at least one —O— heteroatom. Examples of HFEs include, mono-, di-, tri-, and poly-alkoxy-substituted perfluoroalkanes and á-, â-, and ù-substituted hydrofluoroalkyl ethers. Specific examples include the hydrofluoroether, methoxynonafluorobutane, and isomeric mixtures thereof.

HFCs are generally fluorinated hydrocarbons where the carbon backbone consists entirely of carbon atoms, or does not contain an —O— heteroatom. Examples of HFCs include, linear and branched hydrofluorobutanes, hydrofluoropentanes, hydrofluorohexanes, hydrofluoroheptanes, as well as and fluorinated cyclopentanes. Numerous HFCs are commercially available, for example, under the names Vertrel® (E. I. DuPont de Nemours, Wilmington, Del.) and Zeorora-H® (Nippon Zeon, Tokyo, Japan).

Examples of perfluorinated amines and perfluorinated cyclic ethers include, perfluoro-4-methylmorpholine, perfluorotriethylamine, perfluoro-2-ethyltetrahydrofuran, perfluoro-2-butyltetrahydrofuran, perfluoro-4-isopropylmorpholine, perfluorodibutyl ether, perfluorotripropylamine, perfluorotributylamine, perfluorodihexyl ether, perfluoro[2-(diethylamino)ethyl-2-(N-morpholino)ethyl]ether, and n-perfluorotetradecahydrophenanthrene.

HHFEs are generally fluorinated ethers where the carbon backbone also has been substituted with one or more non-fluorine halogen atoms. Examples of HHFEs include perfluoroalkylhaloethers.

The second solvent can also be a mixture of fluorinated solvents, preferably a mixture of a perfluorinated hydrocarbon or a perfluorinated cyclic ether with a HCFC, HFE, HFC or HHFE.

EXAMPLE 1

Z-Tetraol 2000, a highly polar, functionalized perfluoropolyether lubricant manufactured by Solvay Solexis, was fractionated via liquid/liquid extraction using methyl alcohol and perfluorohexane (Fluorinert® FC-72 from 3M). The fractionation was achieved by first dissolving 3.0 grams of Z-Tetraol into 4.6 grams of methyl alcohol solvent. The Z-Tetraol/methyl alcohol solution was carefully dispensed on top of a perfluorohexane solvent layer inside a liquid/liquid extractor. Liquid perfluorohexane was then continuously passed through the Z-Tetraol/methyl alcohol solution by heating a round bottomed flask charged with perfluorohexane to reflux and condensing the perfluorohexane vapors above the Z-Tetraol/methyl alcohol solution. The condensing perfluorohexane was allowed to pass through the Z-Tetraol/methyl alcohol solution for eight hours. During the extraction, that fraction of the Z-Tetraol soluble in the less-polar perfluorohexane collected in the refluxing perfluorohexane solvent and that fraction more soluble in the polar methanol remained in the methanol solution.

After the extraction period, the methanol solution was isolated via decanting or via pipette. The methanol soluble fraction was isolated via evaporation of the methanol and the perfluorohexane soluble fraction was isolated via evaporation of the perfluorohexane. Each solvent evaporation was achieved via heating under an IR lamp while passing dry nitrogen gas over the solvent.

After evaporation of the solvents, the two fractions of Z-Tetraol were characterized via 19F NMR and High Resolution Thermogravimetric Analysis (HiResTGA). These characterizations revealed the separation of a highly polar fraction in the polar solvent methyl alcohol and the less polar fraction in the less polar solvent perfluorohexane. 37% of the original Z-Tetraol was soluble in the methyl alcohol and 63% was extracted by the perfluorohexane. The more polar alcohol-soluble fraction had a significantly lower number average molecular weight compared to the less polar perfluorohexane-soluble fraction via NMR (Table 1).

TABLE 1

|  | Virgin Z-Tetraol | Methanol Soluble Z-Tetraol | Perfluorohexane Soluble Z-Tetraol |
| --- | --- | --- | --- |
| Number Average Molecular wt. | 2150 | 1470 | 2880 |
| End Group Ratio Z-Tetraol:Z-Dol | 1.75:0.25 | 1.90:0.10 | 1.61:0.39 |

As shown in Table 1, the liquid/liquid extraction provides a separation of a more polar, lower molecular weight distribution of Z-Tetraol from a less polar, higher molecular weight distribution of Z-Tetraol. Also obtained in the fractionation is an enrichment of the Z-Tetraol end group functionality in the more polar fraction as those molecules containing Z-Dol end groups tend to dissolve into the less polar solvent.

Figure 2:
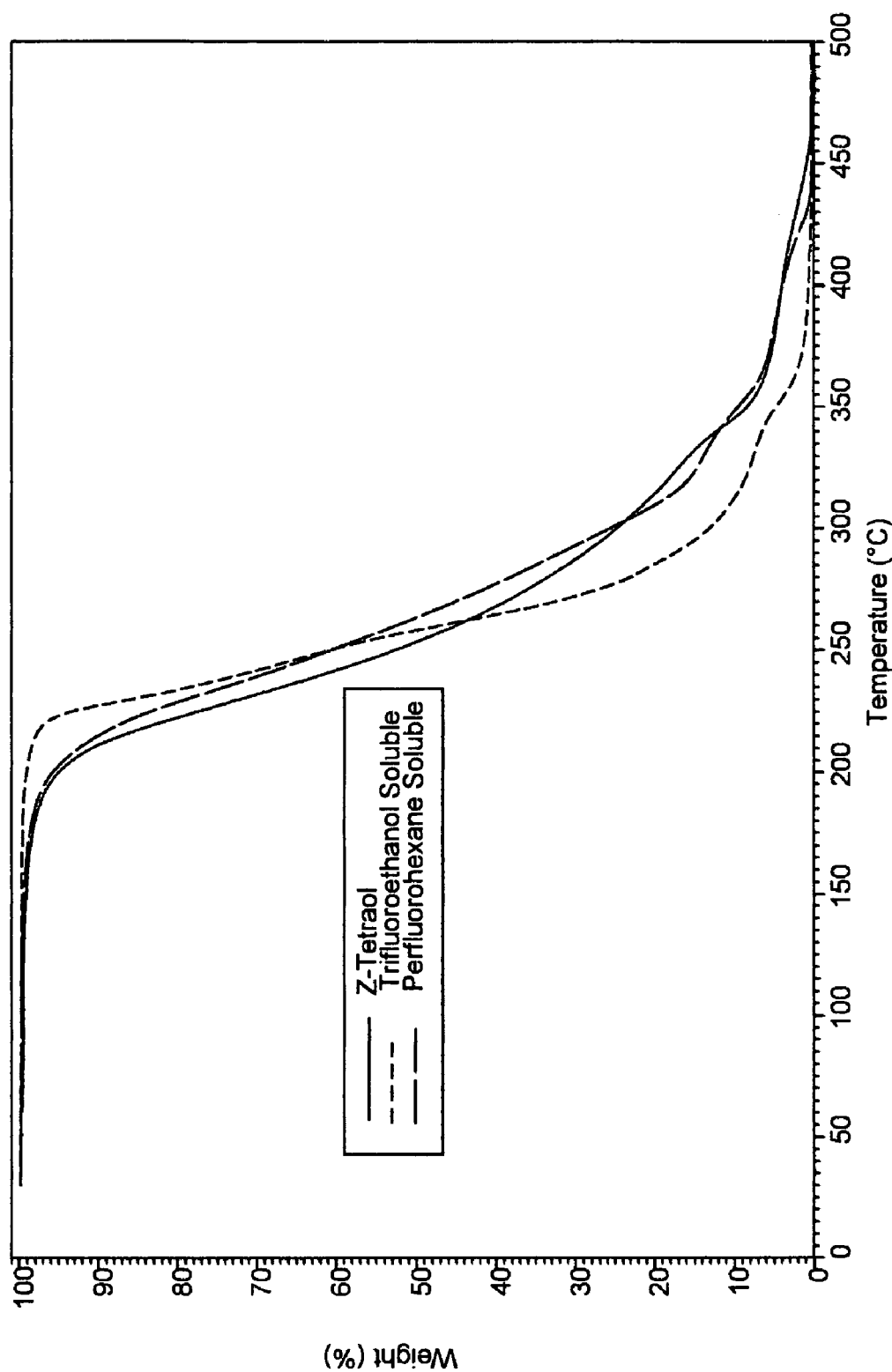
FIG. 2 is a thermogravimetric analysis curve comparing the molecular weight distribution of the virgin Z-Tetraol, the trifluoroethanol-soluble fraction and the perfluorohexane-soluble fraction for Example 2.

HiResTGA was used to compare the molecular weight distribution of the virgin Z-Tetraol, the methanol-soluble fraction and the perfluorohexane-soluble fraction. As indicated in the TGA curve of FIG. 1, the weight loss profiles are consistent with the 19F NMR data reflecting a more volatile molecular weight fraction for the methanol-soluble Z-Tetraol and less volatile molecular weight fraction for the perfluorohexane-soluble Z-Tetraol. The steeper slope of the data for the methanol-soluble Z-Tetraol shown in FIG. 2 also shows a tighter molecular weight range for the methanol-soluble fraction.

EXAMPLE 2

Z-Tetraol 2000, a highly polar, functionalized perfluoropolyether lubricant manufactured by Solvay Solexis was fractionated via liquid/liquid extraction using 2,2,2-trifluoroethanol and perfluorohexane (Fluorinert® FC-72 from 3M). The fractionation was achieved by first dissolving 3.7 grams of Z-Tetraol into 4.8 grams of 2,2,2-trifluoroethanol solvent. The Z-Tetraol/trifluoroethanol solution was carefully dispensed on top of a perfluorohexane solvent layer inside a liquid/liquid extractor. Liquid perfluorohexane was then continuously passed through the Z-Tetraol/methyl alcohol solution by heating a round bottomed flask charged with perfluorohexane to reflux and condensing the perfluorohexane vapors above the Z-Tetraol/methyl alcohol solution. The condensing perfluorohexane was allowed to pass through the Z-Tetraol/methyl alcohol solution for five hours. During the extraction, that fraction of the Z-Tetraol soluble in the less-polar perfluorohexane collected in the refluxing perfluorohexane solvent and that fraction more soluble in the polar methanol remained in the trifluoroethanol solution.

After the extraction period, the trifluoroethanol solution was isolated via decanting or via pipet. The trifluoroethanol soluble fraction was isolated via evaporation of the trifluoroethanol and the perfluorohexane soluble fraction was isolated via evaporation of the perfluorohexane. Each solvent evaporation was achieved via heating under an IR lamp while passing dry nitrogen gas over the solvent.

After evaporation of the solvents, the two fractions of Z-Tetraol were characterized via 19F NMR and High Resolution Thermogravimetric Analysis (HiResTGA). These characterizations revealed the separation of a highly polar fraction in the polar solvent trifluoroethanol and the less polar fraction in the less polar solvent perfluorohexane. 6% of the original Z-Tetraol was soluble in the trifluoroethanol and 94% was extracted by the perfluorohexane. The more polar alcohol-soluble fraction had a significantly lower number average molecular weight compared to the less polar perfluorohexane-soluble fraction via NMR (Table 2).

TABLE 2

|  | Virgin Z-Tetraol | Trifluoroethanol Soluble Z-Tetraol | Perfluorohexane Soluble Z-Tetraol |
| --- | --- | --- | --- |
| Number Average Molecular wt. | 2150 | 1210 | 2200 |
| End Group Ratio Z-Tetraol:Z-Dol | 1.75:0.25 | 1.97:0.03 | 1.71:0.29 |

As shown in Table 2, compared to the perfluorohexane/methyl alcohol extraction described in Example 1, the liquid/liquid extraction from the more polar trifluoroethanol (versus methyl alcohol) provides a separation of an even more polar, lower molecular weight distribution of Z-Tetraol from a less polar, higher molecular weight distribution of Z-Tetraol. Also obtained in the fractionation is a greater enrichment of the Z-Tetraol end group functionality in the more polar fraction as fewer of those molecules containing Z-Dol end groups tend to dissolve into the trifluorethanol.

HiResTGA was used to compare the molecular weight distribution of the virgin Z-Tetraol, the trifluoroethanol-soluble fraction and the perfluorohexane-soluble fraction. As indicated in the TGA curve of FIG. 2, the weight loss profiles are consistent with the 19F NMR data reflecting a more volatile molecular weight fraction for the trifluoroethanol-soluble Z-Tetraol and less volatile molecular weight fraction for the perfluorohexane-soluble Z-Tetraol. The steeper slope of the data for the trifluoroethanol-soluble Z-Tetraol shown in FIG. 2 also shows a tighter molecular weight range for the trifluoroethanol-soluble fraction.

While the present invention has been particularly shown and described with reference to the preferred embodiments, it will be understood by those skilled in the art that various changes in form and detail may be made without departing from the spirit and scope of the invention. Accordingly, the disclosed invention is to be considered merely as illustrative and limited in scope only as specified in the appended claims.

What is claimed is:

1. A method for separating a perfluorinated polyether (PFPE) having di-hydroxyl end groups from a mixture of a first PFPE having hydroxyl end groups and a second PFPE having di-hydroxyl end groups, each of the first and second PFPEs having a distribution of molecular weights in the mixture, the method comprising:
   providing an alcohol solvent and a fluorinated solvent;
   mixing the PFPE mixture with the solvents in a liquid/liquid extractor to concentrate lower-molecular-weight second PFPE in the alcohol solvent and first PFPE and higher-molecular-weight second PFPE in the fluorinated solvent;
   after mixing, separating the solvents; and
   evaporating the alcohol solvent to substantially isolate lower-molecular-weight second PFPE from the mixture.

2. The method of claim 1 wherein the alcohol is methanol.

3. The method of claim 1 wherein the alcohol is trifluoroethanol.

4. The method of claim 1 wherein the fluorinated solvent is selected from perfluorinated hydrocarbons, hydrochlorofluorocarbons, hydrofluoroethers, hydrofluorocarbons, hydrohalofluoroethers, perfluorinated amines and perfluorinated cyclic ether.

5. The method of claim 4 wherein the fluorinated solvent is a perfluorinated hydrocarbon.

6. The method of claim 5 wherein the fluorinated solvent is perfluorohexane.

7. The method of claim 1 wherein the second solvent is a mixture of a perfluorinated hydrocarbon or a perfluorinated cyclic ether with a hydrochlorofluorocarbon, a hydrofluoroether, a hydrofluorocarbon, or a hydrohalofluoroether.

8. The method of claim 1 wherein said second PFPE has the general structural formula:

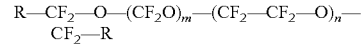
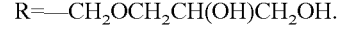

where m and n are integers and
R=—CH$_2$OCH$_2$CH(OH)CH$_2$OH.

9. The method of claim 1 wherein each of the first and second PFPEs has the general structural formula:

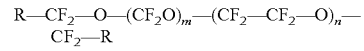

where m and n are integers, and where R=—CH$_2$OH for the first PFPE, and
R=—CH$_2$OCH$_2$CH(OH)CH$_2$OH for the second PFPE.

* * * * *